United States Patent [19]

Powers et al.

[11] 4,182,160
[45] Jan. 8, 1980

[54] HYDROSTATIC PIPE TESTER

[75] Inventors: Joseph E. Powers; Ranoldo H. Grimoldi, both of Napa, Calif.

[73] Assignee: Kaiser Steel Corporation, Oakland, Calif.

[21] Appl. No.: 929,429

[22] Filed: Jul. 31, 1978

[51] Int. Cl.² ............................................. G01M 19/00
[52] U.S. Cl. ....................................................... 73/49.5
[58] Field of Search ........................ 73/49.5, 49.1, 40.5

[56] References Cited

U.S. PATENT DOCUMENTS

| | | | |
|---|---|---|---|
| 2,183,974 | 12/1939 | Richardson | 73/51 |
| 2,493,061 | 1/1950 | Devine | 73/37 |
| 2,755,661 | 7/1956 | Lorant | 73/49.5 |
| 2,959,955 | 11/1960 | Pasquale | 73/49.1 |
| 3,460,376 | 8/1969 | Kemp | 73/49.5 |
| 3,566,675 | 3/1971 | Ledebur | 73/49.5 |
| 3,710,628 | 1/1973 | Horton | 73/49.5 |
| 4,086,806 | 5/1978 | Covey | 73/49.5 |

FOREIGN PATENT DOCUMENTS 1139669  11/1962  Fed. Rep. of Germany ............ 73/49.5

Primary Examiner—S. Clement Swisher
Assistant Examiner—Denis E. Corr
Attorney, Agent, or Firm—Naylor, Neal & Uilkema

[57] ABSTRACT

A tester having a pair of bolsters connected together by a tension framework and adapted to receive therebetween a pipe to be tested. One of the bolsters is movable along the framework to accommodate pipes of different lengths and locking pins are provided to secure the movable bolster at select positions along the length of the framework. The pins are received in openings having enlarged portions to facilitate pin insertion and reduced portions to provide confronting surface-to-surface contact between the pins and the openings upon test loading. The movable bolster carries its own pumping facility to withdraw water from a sump disposed beneath the tester and pump the water through a charging conduit on the bolster and into the pipe being tested. A stripper extends through the charging conduit to selectively remove a pipe from the movable bolster upon completion of a test. Vertically adjustable carriages are provided to support pipes of different diameter in a condition aligned with the bolsters. The carriages support the pipe on rolls mounted for movement about axes extending normal to the longitudinal dimension of the pipes, and brakes are provided to selectively brake the rolls against rotation. The tester supports a pipe being tested in a condition sloping downwardly relative to the movable bolster.

10 Claims, 11 Drawing Figures

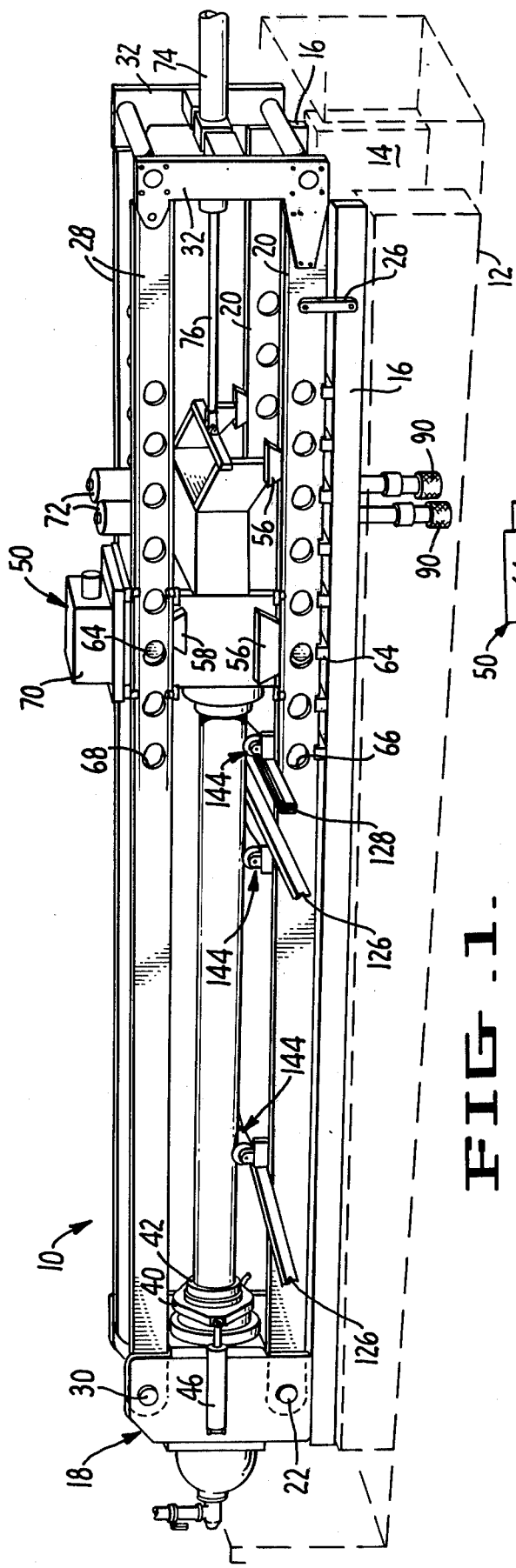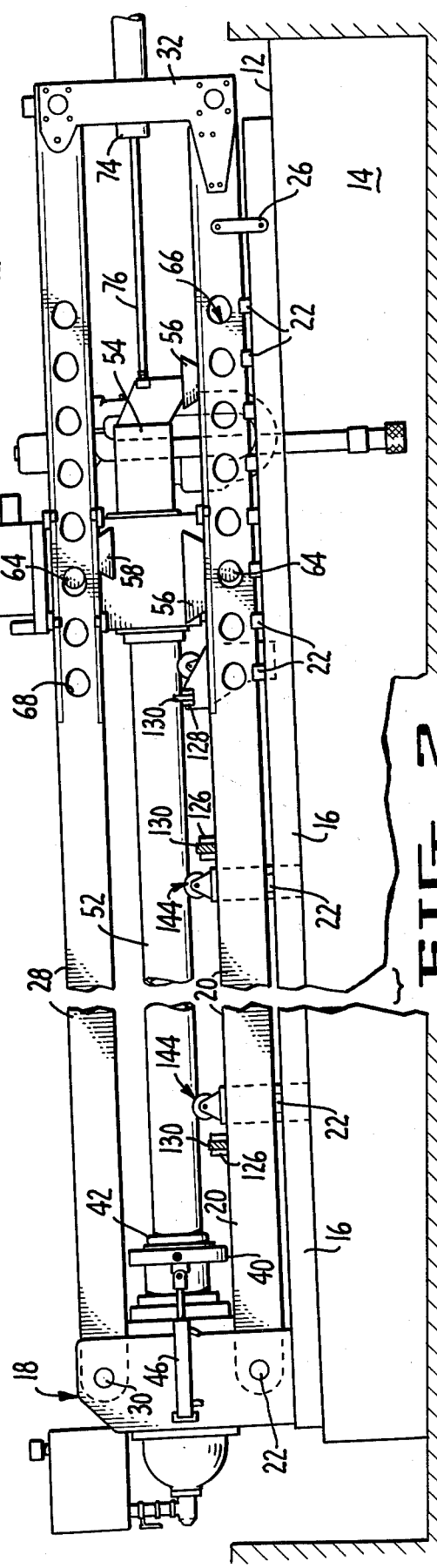

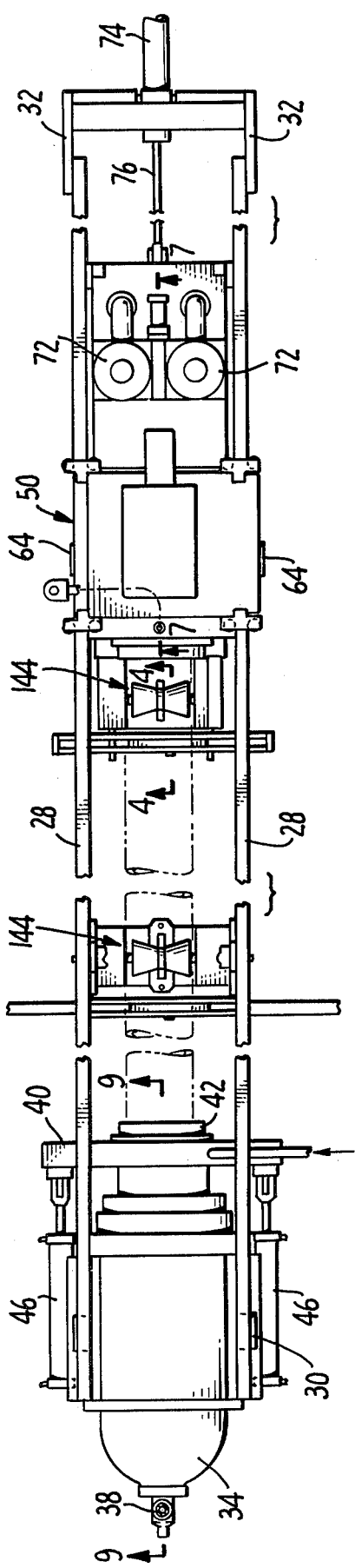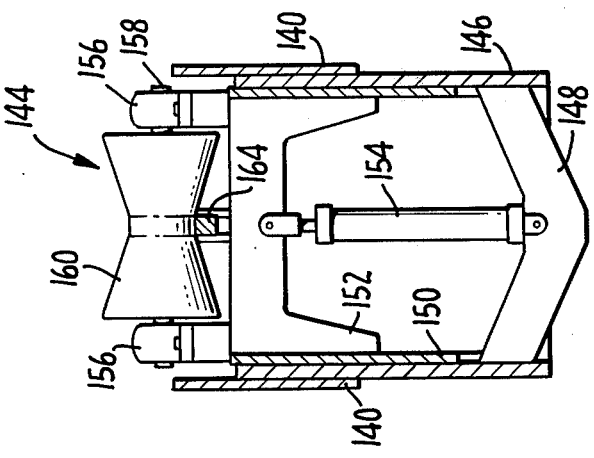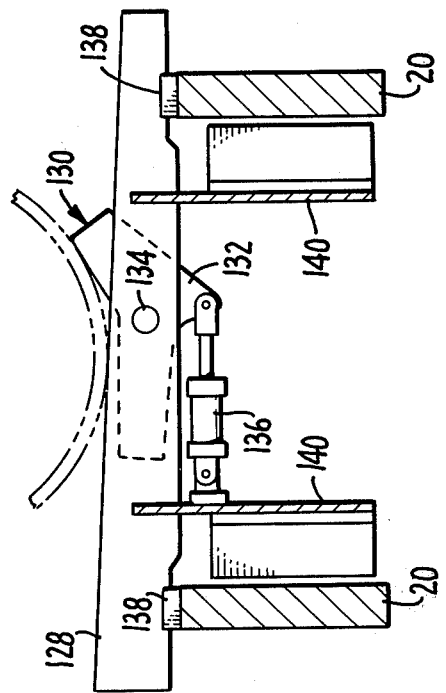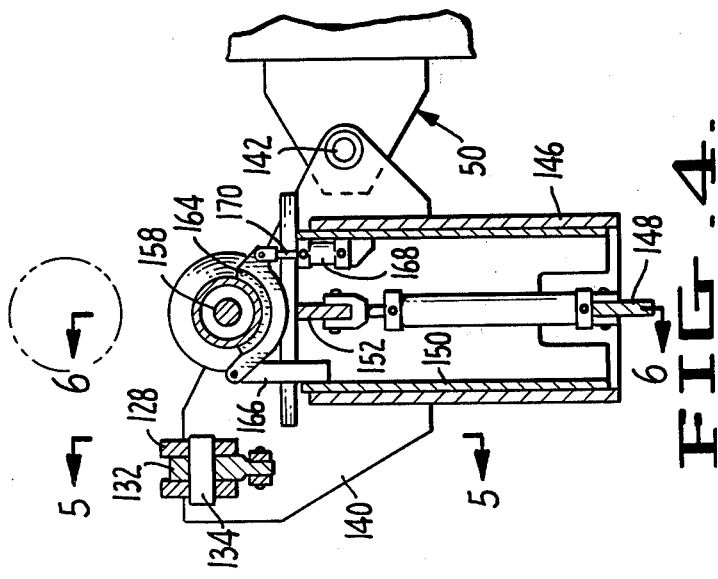

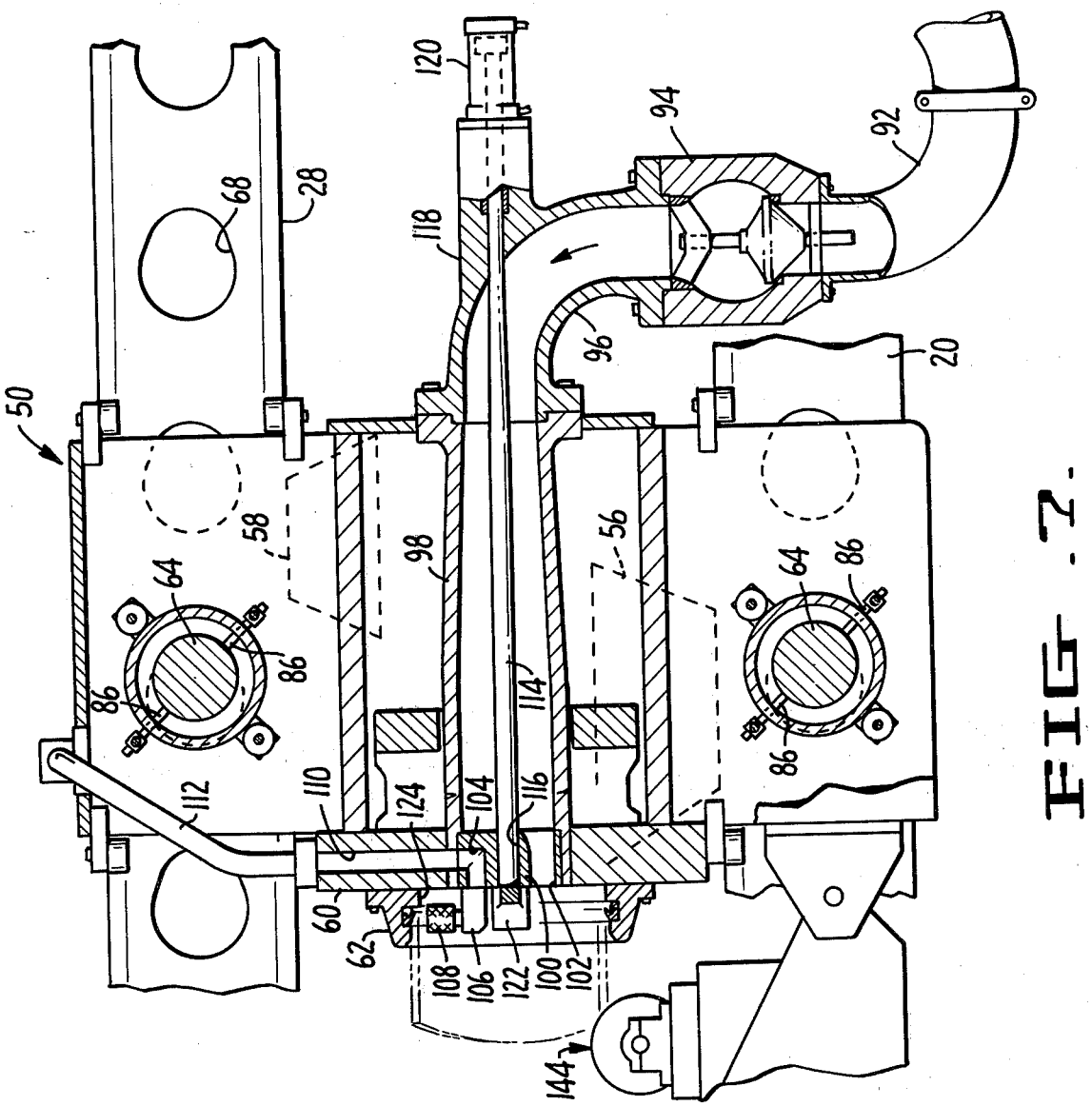
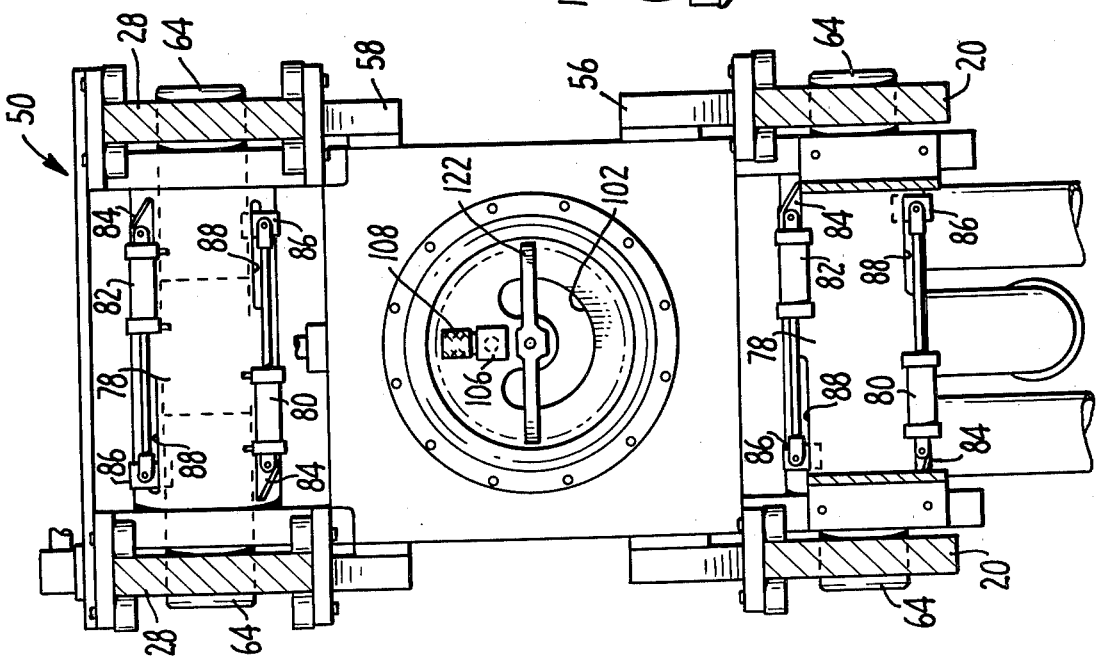

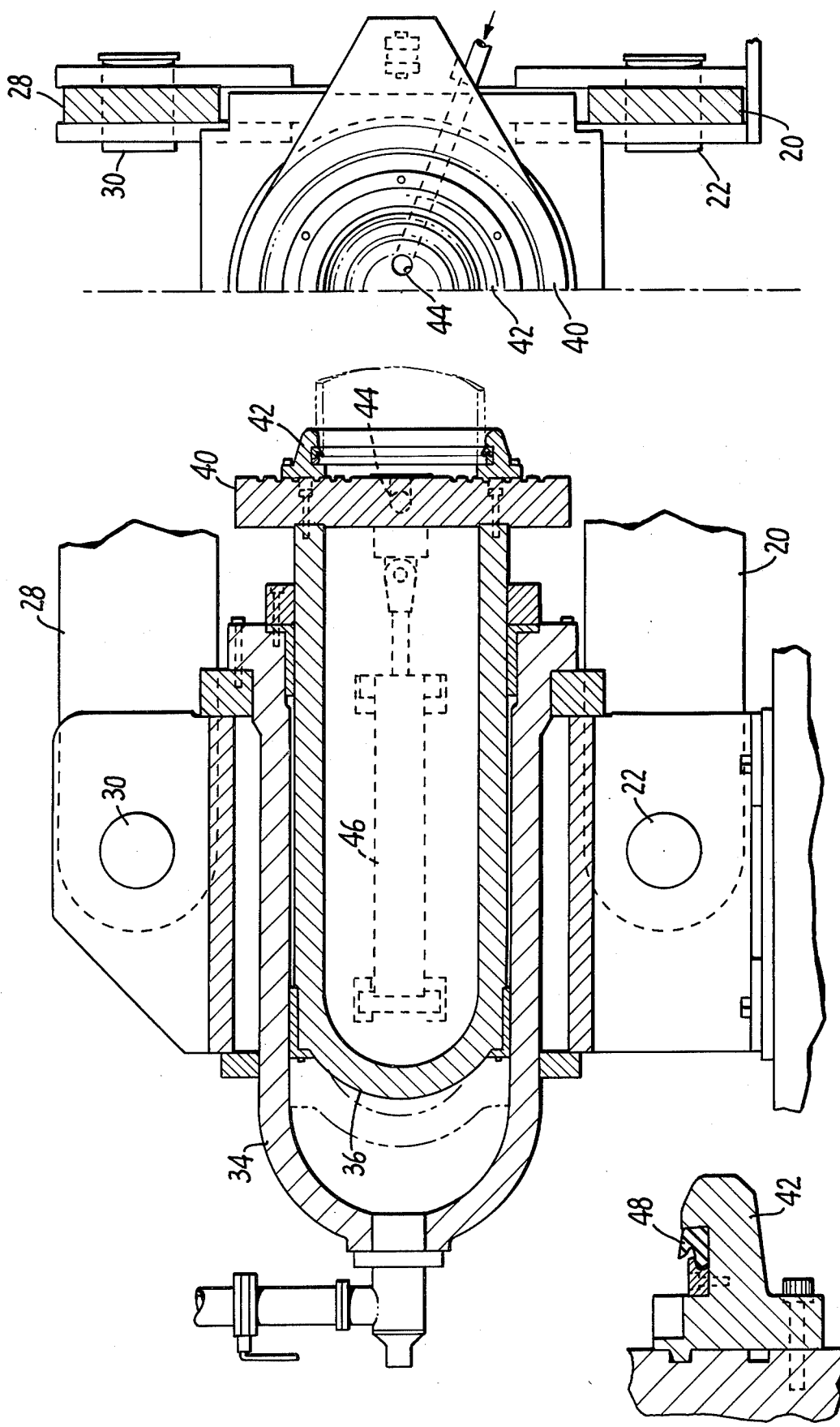

HYDROSTATIC PIPE TESTER

BACKGROUND OF THE INVENTION

The present invention relates to a tester for hydraulically testing the fluid pressure bearing capacity of large diameter pipe and is particularly concerned with such a tester designed for production testing in a pipe mill.

Hydrostatic pipe testers are well known in the prior art. These testers typically operate by capturing the pipe to be tested between a pair of bolsters which seal the ends of the pipe. The pipe is then filled with water at low pressure and, once full, the pipe is subjected to extremely high pressure. The high pressure typically subjects the pipe to stresses approximately equal to 90% of its yield strength. Once a test is complete, the water is drained from the pipe and the pipe is stripped from the bolsters.

Prior art testers have employed movable bolsters to accommodate pipes of different lengths and various means for clamping the bolsters in secure engagement with the pipe being tested and supplying fluid under pressure to the interior of the pipe.

SUMMARY OF THE INVENTION

The present invention is concerned with an improved tester wherein the pipe being tested is filled through means of a pumping facility carried by the tail bolster, thus avoiding the necessity of flexible or extensible conduits between the pumping facility and tail bolster. It is also concerned with improved selectively adjustable pipe supporting carriages, improved locking pin structure for locking a movable tail bolster at different positions along the length of the tension framework of the tester, and a novel supply conduit and stripper arrangement for a bolster.

A principle object of the invention is to provide a tester having the foregoing improved and novel characteristics.

Another object of the invention is to provide such a tester wherein the pipe being tested rolls through the machine, rather than down into the machine. This is particularly advantageous for the production testing of pipe, since it minimizes test cycle time.

A further object of the invention is to provide a tester wherein only one end is attached to a foundation and the remainder of the tester is mounted for free movement relative to the foundation to avoid the imparting of destructive forces to the foundation.

Still another and more specific object of the invention is to provide a tester wherein roller carriages support the pipe being tested and brakes are provided to selectively brake the rollers.

Yet another object of the invention is to provide a tester wherein the movable tail bolster is selectively locked at different positions along the framework of the tester through means of locking pins which cooperate with enlarged receiving openings which facilitate pin insertion and have reduced sections complementally engageable with the pins upon test loading.

The foregoing and other objects will become more apparent when viewed in conjunction with the following detailed description and accompanying drawings.

BRIEF DESCRIPTION OF THE DRAWINGS

FIG. 1 is a perspective view of the tester of the invention, showing a pipe in condition for testing and a phantom line representation of the foundation and sump employed with the tester;

FIG. 2 is a side elevational view of the tester shown in FIG. 1;

FIG. 3 is a top plan view of the tester shown in FIG. 1;

FIG. 4 is a cross-sectional view taken on the plane designated by line 4—4 of FIG. 3, illustrating one of the roller cradles of the invention and the brake employed with that cradle;

FIGS. 5 and 6 are cross-sectional views taken on the planes designated by lines 5—5 and 6—6, respectively, of FIG. 4.

FIG. 7 is a cross-sectional view taken on the plane designated by line 7—7 of FIG. 3, illustrating the high volume water supply conduit and the stripper construction of the tester tail bolster;

FIG. 8 is an elevational view of the left-hand side of the tail bolster shown in FIGS. 7;

FIG. 9 is a cross-sectional view of the tester head bolster, taken on the plane designated by line 9—9 of FIG. 3;

FIG. 10 is an enlarged cross-sectional view, with parts thereof broken away, illustrating the pipe engaging flange of the head bolster shown in FIG. 9; and, FIG. 11 is an elevational view of the right-hand side of the head bolster shown in FIG. 9, with parts thereof broken away and shown in section.

DESCRIPTION OF THE PREFERRED EMBODIMENT

Referring to FIG. 1, the tester is designated therein in its entirety by the numeral 10. The tester is supported on a concrete foundation 12 defining a water sump area 14. A base structure comprised of side frame members 16 is anchored to the top of the foundation 12 and fixedly supports at one end thereof the ram end bolster 18 of the tester.

A pair of lower tension bars 20 are pivotally secured to the ram end bolster 18 by pins 22 and extend therefrom over the side frame members 16. Bearing pads 24 support the bars 20 for slidable movement on the frame members 16 and links 26 connect the bars and frame members, while permitting the bars to slide on the frame members. A pair of upper tension bars 28 are pivotally secured at one end thereof to the bolster 18 by pins 30 and extend therefrom over the bars 20. Upright frame members 32 connect the distal ends of the bars 20 and 28 together and maintain the bars in spaced parallel relationship to one another.

The bolster 18 carries a main ram assembly comprising (see FIG. 9): a high pressure cylinder 34 having a piston 36 received therein; a check valve assembly 38 communicating with the interior of the cylinder 34 and a source of high pressure fluid (not illustrated); a plate 40 secured to one end of the piston 36 and carrying a collar 42 for sealing engagement with the outer periphery of the pipe being tested; a high pressure conduit 44 extending radially through the plate 40 and discharging through a mid-portion thereof within the peripheral confines of the collar 42; and, a pair of double acting hydraulic cylinders 46 secured between the side members of the fixed bolster 18 and the plate 40. The collar 42 carries a resilient lip (see FIG. 10) disposed for sealing engagement with the outer periphery of the pipe being tested. The double acting cylinders 46 are provided to facilitate the rapid extension and retraction of the piston 36 relative to the cylinder 34. During such extension and retraction, pressure within the cylinder 34 is relieved.

The basic structure and mode of operation of the aforedescribed bolster ram assembly is known in the art and does not form part of the present invention. By this, it is meant that the means for extending and retracting the cylinder and piston assembly 34 and 36 and supplying high pressure fluid to the cylinder is not unique to the present invention.

The tail bolster of the tester, designated in its entirety by the numeral 50, is movably supported on the tension bars 20 and 28 for movement toward and away from the ram end bolster 18 to accommodate pipes of different lengths. An example of such a pipe is shown in the drawings and designated by the numeral 52. As illustrated, the pipe 52 has a length intermediate the minimum and maximum lengths which the tester is designed to accommodate.

The basic elements of the tail bolster 50 comprise: a frame 54 slidably supported on the bars 20 by bearing pads 56 and having upper bearing pads 58 slidably engaged with the tension bars 28; a plate 60 on the side of the frame in apposition to the plate 40 of the ram end bolster 18; a collar 62 mounted on the plate 60 for engagement with the outer peripheral surface of the pipe being tested; selectively extensible and retractable locking pins 64 carried by the frame 54 for engagement with openings 66 and 68 in the tension bars 20 and 28, respectively; an hydraulic pump 70 carried by the frame 54 to supply hydraulic fluid to actuating cylinders for the pins 64; and, high volume low pressure pumps 72 carried by the frame 54 to pump water into a pipe being tested.

With the pins 64 retracted, the tail bolster 50 may be selectively moved toward or away from the ram end bolster 18 by an hydraulic cylinder 74 mounted on the frame members 32 and having its piston rod 76 connected to the frame 54. In the preferred embodiment, the cylinder 74 is of the double acting type so that a single cylinder may be used to move the bolster 50 toward or away from the bolster 18.

The mechanism for extending and retracting the pins 64 can be seen from FIG. 8. This mechanism comprises tubular members 78 supported by the frame 54 and slidably receiving therein the pins 64; a first pair of hydraulic cylinders 80 connected between the tubular members 78 and the right hand locking pins 64 (as viewed in FIG. 8); and, a second pair of hydraulic cylinders 82 connected between the tubular members 78 and the left hand pins 64 (as viewed in FIG. 8). The cylinders 80 and 82 are connected to the tubular members 78 by ears 84. The piston rods of the cylinders are connected to the respective pins by laterally extending plate elements 86 secured to the pins and extending therefrom through slots 88 formed in the tubular members 78. In operation, extension of the cylinders 80 and 82 functions to extend the pins 64 and retraction of the cylinders functions to retract the pins. Conduits and suitable valving means (not illustrated) are provided to selectively supply hydraulic fluid to the cylinders 80 and 82 from the pump 70.

The openings 66 and 68 are of a dual diameter configuration with large diameter segments of a cross section greater than the pins 64 and reduced diameter segments having one side of a shape corresponding to the peripheral shape of, i.e., congruent with, the pins. The purpose of this dual diameter configuration is to provide an enlarged segment through which the pins can be easily inserted and a reduced diameter segment adapted for snug complemental engagement with the pins when the pins are subjected to loading in response to the pressurization of a pipe being tested. As shown in FIG. 2, the pins 64 are received in complemental engagement with the reduced diameter segments of the openings. In the preferred mode of operation, the enlarged segment portions of the openings would be generally aligned with the pins during pin extension and then, after pin extension, the cylinder 74 would be retracted somewhat to move the pins into preloaded engagement with the reduced diameter segments of the openings. This mode of operation would assure that the pins would not be shock loaded upon the pressurization of a pipe being tested.

Water for the tester is charged into the pipe being tested through means of the high volume water supply system carried by the tail bolster 50. In addition to the pumps 72, this system comprises a pair of inlet pipes 90 which depend from the bolster and extend into the sump area 14. It should be appreciated that the sump 14 is normally filled with water to a level above the lower ends of the inlet pipes. These lower ends are open and, as shown, provided with screens to prevent foreign objects from being drawn thereinto. The pumps 72 draw water into the pipes 90 and discharge it through the tail bolster 50 and into the pipe being tested.

The structure of the water charging conduit system within the tail bolster 50 can be seen from FIG. 7. This structure includes; a supply pipe 92 connected to the output side of the pumps 72; a check valve 94 connected to the outlet end of the pipe 92; an elbow conduit 96 connected to the downstream end of the check valve 94; a conduit 98 connected to the downstream side of the conduit 96 and extending therefrom through the plate 60 in generally concentric relationship to the collar 62; and, a plug 100 in the downstream end of the conduit 98, said plug having a semicircular discharge passage 102 in the lower portion thereof and a vent passage 104 in the upper portion thereof. The passages 102 and 104 are disposed so as to communicate with the interior of a pipe engaged within the collar 62. In operation, water is charged into such a pipe through the discharge passage 102 and, simultaneously with the charging, air is vented from the pipe through the passage 104. An angle conduit 106 with a screen 108 thereon is connected to a passage 104 so as to vent air from the upper extremity of the pipe being tested. The downstream end of the passage 104 communicates with a passage 110 extending through the plate 60, which passage in turn is connected to a vent pipe 112.

The conduit system within the tail bolster 50 also includes a mechanism for stripping pipe from the collar 62 after the completion of a test. This mechanism comprises: a rod 114 extending axially through the conduit 98, said rod extending slidably through a passage 116 therefor in the plug 100 and a packing box 118 on the elbow conduit 96; an hydraulic cylinder 120 mounted on the packing box 118 and connected to the rod 114 to selectively impart axial movement to the rod; and, a stripper bar 122 connected to the end of the rod 114 and disposed within the peripheral confines of the collar 62. The bar 122 extends diametrically across the inside of the collar 92 and has narrowed distal ends disposed to engage beneath the end of a pipe engaged by the collar. A shoulder 124 is formed on the collar 62 for engagement with the distal end with a pipe engaged by the collar. The shoulder is so proportioned as to permit the distal ends of the stripper bar 22 to be disposed between the plate 60 and the end of the pipe.

In operation of the tester, the stripper mechanism is employed to strip a pipe from the tail bolster 50 after such a pipe has been tested and disengaged from a ram end bolster 18. Stripping is achieved by simply actuating the cylinder 120 to extend the rod 114 and force the bar 122 against the end of the pipe. The bar, in turn, forces the pipe out of the collar 62. The hydraulic actuating fluid for the cylinder 120 may be provided by the pump 70. Suitable valving means is provided to selectively actuate the cylinder.

In the testing of pipe, pipe is rolled into one side of the tester, clamped between the bolsters and subjected to testing pressure, and then rolled out the other side of the tester. This "roll-through" operation ideally suits the tester for production testing in a pipe mill. It also greatly facilitates the handling of large diameter pipe (e.g., 24" to 56") in that it is not necessary to lower pipe into the tester.

As viewed in FIG. 1, pipe is rolled into the tester from the front on ramps 126 and 128 and, once within the tester, is stopped on the ramps by pipe feed stops 130. A pipe feed stop is provided for each of the ramps. The detailed construction of the stops may be seen from FIG. 5 wherein it can be seen that each stop comprises an angle shaped arm 132 pivotally supported between the side members of the ramp by a pin 134. An hydraulic cylinder 136 is connected between the ramp supporting structure and an extension on the arm 132 to selectively move the arm between the solid and phantom line positions shown in FIG. 5. In the solid line position, the arms 132 function to stop a pipe fed into the tester in a position in vertical alignment with the bolsters. In the phantom line position, the arms 130 function to "kick" a pipe out of the tester. The inclined disposition of the ramps 126 and 128 facilitates the rolling of pipe thereover under the influence of gravity.

The ramps 126 are supported on the lower tension bars and do not move relative thereto. The ramp 128 is also supported on the bars 20, but is disposed for slidable movement thereover and provided with bearing pads 138 to facilitate such movement (see FIG. 5). The purpose of the movable mounting for the ramp 128 is to permit the ramp to move with the tail bolster 50. From FIG. 4, it will be seen that the ramp 128 is carried by plates 140 pivotally secured at one end thereof to the tail bolster by a pin connection 142. FIG. 5 shows that one end of the cylinder 136 is connected to one of the plates 140.

Once a pipe is rolled into the tester and engaged by the stops 130, carriages 144 within the tester are elevated to engage the undersurface of the pipe and move the pipe into a condition axially aligned with the bolsters 18 and 50. In the embodiment illustrated, two of these carriages (the left most carriages shown in FIGS. 1 and 2) are mounted to the lower tension bars 20 and a third carriage is mounted between the plates 140 carried by the tail bolster 50.

The detailed construction of the carriages 144 can be seen from FIGS. 6 wherein the carriage carried by the tail bolster 50 is illustrated. Each carriage comprises: a vertically extending open ended support box 146 secured to the supporting members therefor (the plate members 140 in the FIGS. 4 and 6 embodiment); cross member 148 fixedly secured across the lower end of the box 146; a slide box 150 slidably received within the box 146 for vertical movement therein; an upper cross member 152 fixed to and extending across the slide box 150 in vertical alignment with the cross member 148; an hydraulic cylinder 154 connected between the cross members 148 and 152 to selectively raise and lower the cross member 152 and the slide box 150 connected thereto; a pair of trunions 156 mounted on the top of the slide box 150, said trunions having a shaft 158 journalled therebetween which carries a V-shaped cradle roll 160 having a flat cylindrical central section 162; a brake shoe 164 pivotally supported beneath the flat cylindrical section 162 on a support 166 fixed to one side of the slide box 150; and, an hydraulic cylinder 168 connected to one side of the slide box 150 in alignment with the shoe 164, said cylinder having the piston rod 170 thereof pivotally connected to the end of the shoe 164 opposite that connected to the support 60 and being selectively extensible and retractable to move the shoe 164 into and out of braking engagement with the cylindrical section 162 of the roll 160.

OPERATION

In operation, the distance between the ram end bolster 18 and the tail bolster 50 is first adjusted to accommodate the length of pipe to be tested. This length is chosen so as to be sufficiently greater than the length of the pipe so that the pipe may be easily rolled into the tester and the ram end bolster may then be extended to clamp the pipe between the ram end and tail bolsters. Adjustment is achieved by first retracting the locking pins 64 and then adjusting the position of the tail bolster through means of the cylinder 74. Once the tail bolster is adjusted to the desired position, the locking pins 64 are extended through the openings 66 and 68 in apposition thereto and the pins are then drawn into the reduced diameter portions of the openings by moving the tail bolster with the cylinder 74.

To prepare the tester for initial receipt for the pipe to be tested, the cylinders 46 are retracted to retract the ram end bolster and the cylinders 154 are retracted to lower the carriage rolls 160. Final preparation of the receipt of a new length of pipe to be tested also entails extending the cylinders 136 to move the stops 130 to the extended condition (i.e., then solid line position shown in FIG. 5).

With the tester adjusted and conditioned for the receipt of a pipe to be tested, the pipe is rolled into the tester on the ramps 126 and 128 to the point where it is engaged and stopped by the stops 130. Once so stopped, the carriage control is activated to raise the carriages 144 to a position wherein a pipe is axially aligned with the bolsters. Suitable control means (not illustrated) is provided to automatically adjust the operation of the carriages to establish such alignment. Once the pipe is aligned with the bolsters, the ram end bolster is extended through means of the cylinders 46 to force the bolster into engagement with the pipe and, in turn, force the pipe into engagement with the tail bolster. During the latter operation, the rolls 160 are in the un-braked condition so as to permit the pipe to move freely in response to the extension of the ram end bolster.

After engagement of the pipe by the bolsters, the pipe is filled with water through means of the high volume pumping facility carried by the tail bolster 50. This draws water from the sump 14 and discharges it into the pipe, simultaneously with the venting of the pipe. Once the pipe is completely full, the supply of high volume water thereto by the pumping facility on the tail bolster is terminated and the check valve 94 and a closure valve in the vent line 112 are closed. The pipe is then subjected to high test pressure by first pressurizing the cylinder 34 and then applying high pressure to the fluid within the pipe through means of the high pressure conduit 44 in the ram end bolster.

After the pipe has been pressure tested to the desired extent, the pressure to the cylinder 34 and the high pressure conduit 44 is terminated and the cylinders 46 are retracted to retract the ram end bolster out of engagement with the pipe. During the latter operation, the brake shoes 164 of the carriages 144 are extended to brake the rolls 160, and thus, restrain the pipe being tested against axial movement in response to retraction of the ram end bolster. Disengagement of the ram end bolster from the pipe permits the water in the pipe to discharge therefrom and spill back into the sump 14. Such discharge is facilitated by the inclined disposition of the tester which can be seen from FIGS. 1 and 2. As there shown, it will be seen that the end of the tester carrying the tail bolster is slightly elevated relative to that carrying the ram end bolster.

After the ram end bolster is disengaged from the pipe being tested, the brake shoes 164 are released and the stripping mechanism within the tail bolster is activated through means of the cylinder 120 to force the pipe out of the collar 62 carried by the tail bolster. At this point, the pipe is free from the bolster and the carriages 144 are lowered to lower the pipe back onto the ramps 126 and 128. With the pipe so lowered, it is then ejected from the tester by retracting the cylinders 136 to kick the pipe to the right (as viewed in FIG. 5).

In the production testing of pipe within a mill, testing is generally carried out on a run (i.e., plurality) of pipe sections of the same length and diameter. The tail bolster would only be adjusted at the beginning of such a run and would remain in the same position throughout the run. The carriages 144 are ideally provided with automatic control means so that each pipe section within a run will be elevated to the same position, without the need of readjustment. The phantom line representation of the roll in FIG. 4 is intended to depict the position which the roll would assume when in such an elevated position.

CONCLUSION

From the foregoing detailed description, it is believed apparent that the invention enables the attainment of the objects initially set forth herein. It should be understood, however, that the invention is not intended to be limited to the illustrated embodiment but rather as defined by the accompanying claims.

What is claimed is:

1. A tester for hydraulically testing the internal fluid pressure bearing capacity of a pipe, said tester comprising, in combination: a foundation defining an open topped elongate sump; a tension frame supported on said foundation and extending longitudinally of said sump; a head bolster secured to said frame at one end thereof for select sealing engagement with one end of the pipe, said bolster having a high fluid pressure source connected thereto for admitting high pressure fluid into the pipe; a movable bolster carried by the other end of the frame for sealing engagement with the other end of the pipe, said movable bolster being selectively movable longitudinally of the frame to accommodate pipes of different lengths; a pump carried by said movable bolster and having outlet means opening through the bolster, which pump and bolster thereby may be free of flexible and extensible conduits therebetween, so as to charge high volume fluid under pressure into the interior of a pipe engaged by the bolster and inlet means depending therefrom into the sump to withdraw fluid from the sump; and means to selectively close the charge pump against fluid flow when high pressure fluid is admitted into a pipe being tested.

2. A tester according to claim 1 wherein the framework and bolsters are so disposed as to support a pipe being tested in a condition inclined downwardly from the movable bolster to the head bolster, said tester further comprising vent means in the movable bolster disposed to exhaust from the upper extremity of the pipe simultaneously with the admission of high volume fluid thereto by the pump carried by the movable bolster; and means to close said vent means upon the admission of high pressure fluid into a pipe being tested.

3. A tester according to claim 1 further including pipe engaging cradles carried by the framework to support a pipe being tested in a condition aligned with the bolsters, said cradles being elevationally adjustable to accommodate pipes of different diameter and at least certain of said cradles comprising rolls disposed for supporting engagement with the pipe, said rolls being mounted for rotation about axes extending normal to the pipe; and brake means to selectively brake the rolls against rotation.

4. A tester for hydraulically testing the internal fluid pressure bearing capacity of a pipe, said tester comprising: a frame having a pair of spaced longitudinally extending tension members; head and tail bolsters secured to the tension members in spaced relationship to one another for receipt therebetween of a pipe being tested, at least one of said bolsters having means for admitting high pressure fluid into the interior of the pipe; pipe engaging cradles supported between the tension members to support the pipe in a condition aligned with the bolsters, said cradles being elevationally adjustable to accommodate pipes of different diameter and at least certain of said cradles comprising rolls disposed for supporting engagement with the pipe, said rolls being mounted for rotation about axes extending normal to the pipe; and brake means to selectively brake the rolls against rotation.

5. A tester according to claim 4 wherein the frame and bolsters are so disposed as to support a pipe being tested in a condition inclined downwardly in one direction.

6. In a hydro-tester having a longitudinally extensive tension frame member with a bolster member adjustable therealong to accommodate pipes of different lengths, an improved structure for locking the bolster member at select positions along the length of the frame member, said structure comprising: a pin carried by one of said members for select extension and retraction relative to the other of said members; and a plurality of openings formed in the other of said members at spaced locations therealong, said respective openings being disposed for alignment with and receipt of the pin as the bolster member is adjusted relative to the frame member, and wherein each opening comprises an enlarged segment of a cross-section greater than that of the pin whereby the pin can enter said segment even though not in precise alignment therewith and a reduced segment having one side of a shape congruent with the shape of the pin so as to be snugly engageable therewith, said segments being so positioned that the pin may first enter the enlarged segment and then, in response to movement of the bolster member in the direction of normal pipe elongation during testing, be drawn into the reduced segment.

7. In a hydro-tester according to claim 6, the improved structure wherein the pin is of circular cross-section and the one side of the reduced segment of the opening is of an arcuate shape conforming to the circular cross-section of the pin.

8. In a hydro-tester according to claim 6, the improved structure wherein the pin is carried by the bolster member and the openings are formed in the frame member.

9. In a hydro-tester bolster having a flange for sealingly engaging the periphery of a pipe being tested, the improvement comprising: a conduit opening through the bolster to charge fluid into the pipe; a rod extending through the conduit; a stripper arm connected to and extending from the rod within the confines of the flange, said arm being disposed to engage beneath the edge of a pipe engaged by the flange; and, an actuator secured to the rod to selectively impart movement thereto to move the stripper arm against the edge of the pipe and force the pipe out of engagement with the flange.

10. In a hydro-tester bolster according to claim 9, the improvement wherein: the conduit opens through the center of the bolster; the rod extends longitudinally through the conduit; the arm is fixedly secured to and extends radially from the rod; and the actuator comprises an hydraulic cylinder connected to the rod to selectively impart longitudinal movement thereto.

* * * * *